(12) United States Patent
Thurston et al.

(10) Patent No.: US 11,589,497 B1
(45) Date of Patent: Feb. 28, 2023

(54) METHOD FOR PLANTING AGRICULTURAL PRODUCTS

(71) Applicants: Dustin W. Thurston, Pulaski, IL (US);
Blake W. Thurston, Pulaski, IL (US);
Cody A. Goins, Buncombe, IL (US)

(72) Inventors: Dustin W. Thurston, Pulaski, IL (US);
Blake W. Thurston, Pulaski, IL (US);
Cody A. Goins, Buncombe, IL (US)

(*) Notice: Subject to any disclaimer, the term of this patent is extended or adjusted under 35 U.S.C. 154(b) by 0 days.

(21) Appl. No.: 17/195,873

(22) Filed: Mar. 9, 2021

Related U.S. Application Data

(60) Provisional application No. 62/987,560, filed on Mar. 10, 2020.

(51) Int. Cl.
*A01H 1/04* (2006.01)
*A01C 1/04* (2006.01)
*A01H 5/10* (2018.01)

(52) U.S. Cl.
CPC .......... *A01C 1/04* (2013.01); *A01H 5/10* (2013.01)

(58) Field of Classification Search
CPC ............. A01C 1/00; A01C 1/04; A01H 1/04
USPC ........................................................ 47/57.6
See application file for complete search history.

(56) References Cited

U.S. PATENT DOCUMENTS

| 3,561,159 A | 2/1971 | Adams, Jr. |
| 3,996,865 A | 12/1976 | Dwyer |
| 4,780,987 A * | 11/1988 | Nelsen et al. ........... A01C 1/06 |
| 6,209,259 B1 | 4/2001 | Madigan et al. |
| 8,966,814 B2 | 3/2015 | Conrad |
| 2006/0162249 A1 | 7/2006 | Zimmermann et al. |
| 2015/0082479 A1* | 3/2015 | Lauer et al. ....... C12N 15/8209 800/272 |
| 2020/0154644 A1 | 5/2020 | Cox |

FOREIGN PATENT DOCUMENTS

| CN | 108811592 | 11/2018 |
| DE | 102017102081 | 7/2018 |
| KR | 10-2008-0089147 | 10/2008 |
| KR | 10-2016-0061579 | 6/2016 |
| KR | 10-1845435 | 3/2018 |

* cited by examiner

*Primary Examiner* — Keith O. Robinson
(74) *Attorney, Agent, or Firm* — Gardner, Linn, Burkhart & Ondersma LLP

(57) ABSTRACT

A method, a container, and a planting device are provided for improving seedling emergence from seeds through soil and improving yield of plants in a field. The method includes selectively planting two seeds next to one another within the soil to provide sufficient emergence energy so the seedlings emerge together through the soil. One of the seedlings is then selectively destroyed to provide a desired spacing between plants in the field. A capsule is provided to contain plantable agricultural products. The capsule enables uniform and consistent planting plantable agricultural products, enables close proximity planting of multiple plantable agricultural products next to one another, and enables uniform and consistent engagement and dispensing of the seeds by planting equipment. A planting device, defined by a planter plate, is designed to consistently and uniformly plant the capsules containing agricultural products within the field.

5 Claims, 5 Drawing Sheets

METHOD FOR PLANTING AGRICULTURAL PRODUCTS

CROSS REFERENCE TO RELATED APPLICATION

The present application claims priority of U.S. provisional application Ser. No. 62/987,560 filed Mar. 10, 2020, which is hereby incorporated herein by reference in its entirety.

FIELD OF THE INVENTION

The present invention is directed to a method of planting agricultural products such as seeds, and in particular a method of planting for improving emergence through the soil and improving overall yield of a crop.

BACKGROUND OF THE INVENTION

Planters and planting methods provide for planting and spacing of seeds in a field. The agricultural industry continuously seeks improved yields from crops within smaller and smaller areas. A common problem in agriculture is inconsistent spacing during planting which results in decreased yield because the spacing between plants is not optimal. Same-species seeds typically vary somewhat in size and shape, which may cause planting equipment to misshandle some seeds leading to inconsistent spacing during planting, which may result in decreased yield. Soils commonly form a "crust" after planting and before emergence, which can either delay the emergence of a seedling or cause the seedling to die because it cannot break through the soil crust.

SUMMARY OF THE INVENTION

The present invention provides a method, a container or package, and a planting device for improving emergence rates of seedlings and improving yield rates of crops planted in a growth medium, such as field soil. The method provides improved emergence rates by utilizing the emergence energy of at least two seeds emerging together through the soil. The method includes planting multiple seeds adjacent to one another and after emergence of seedlings, selectively destroying at least one of the multiple seedlings to reduce the population of plants to improve yield of the crop. A container or capsule is provided for containing one or more agricultural products, including seeds and optionally fertilizers. The capsule may contain a plurality of seeds having different genetic traits or characteristics (e.g. resistance to certain herbicides, such as ROUNDUP® or LIBERTY® for example). The capsule is particularly useful for planting a plurality of seeds in close proximity to one another. The capsule is also particularly useful for encapsulating a single seed or multiple seeds along with fertilizers or other non-seed products to plant seeds and fertilizers proximate one another as the seeds are planted. A planting device is provided for consistently engaging a container or capsule that encapsulates an agricultural product, and uniformly dispensing the capsules in the soil. The planting device may be a planter plate or disc that includes a vacuum system to facilitate engagement of the container by the plate. The capsule and planting device each provide improvements in plant spacing and planting consistency to provide enhanced yields.

According to one form of the present invention, a method is provided for planting seeds to improve emergence rates of seedlings from the seeds through soil and to improve yield rates from the crop. The method includes planting a first seed at a first location and planting a second seed substantially alongside the first seed at the first location. The proximity of the first seed and the second seed allows the emergence energy of each seed to work together to emerge through the soil. Upon emergence of the first seed into a first seedling and the second seed into a second seedling, the method includes selectively destroying or culling one of the first seedling and the second seedling to reduce the population of plants growing in the field. In this manner, the destroyed seedling is sacrificial to ensure emergence of the desired seed. To facilitate selectively destroying one of the seeds, one of the first seed and the second seed may include a genetic characteristic that is not present in the other seed.

In one aspect, the step of selectively destroying one seedling includes selectively targeting the undesired or less-preferred seedling, which in this case is the seedling lacking the genetic characteristic that is present in the other seed, and selectively destroying the undesired seed/seedling. This may be accomplished by administering an herbicide to the seeds, wherein the seed having the genetic characteristic not present in the other seed is resistant to the administered herbicide. It will be appreciated the selective culling of one of the seedlings may be performed manually, such as by hand, and such manual culling may be facilitated based on distinct visual characteristics of the sacrificial seedling.

In another aspect, the step of selectively destroying one seedling includes selectively targeting a distinct genetic characteristic of the genetic profile of an undesired or less-preferred one of the seedlings. This may be accomplished by applying an herbicide to the seeds, wherein the first seedling has a preferred genetic profile and is resistant to the herbicide based on the first seed's distinct genetic characteristic and the second seedling has a less-preferred genetic profile is not resistant and is therefore susceptible to the herbicide.

According to another form of the present invention, a method is provided for planting seeds to emerge through a soil crust and selectively culling some of the emerged seedlings to optimize yield capacity of the soil. The method includes planting a seed capsule in a soil. The seed capsule contains a first viable plant seed and a second viable plant seed having a unique genetic characteristic not present in the first plant seed. The soil is monitored for seedling growth for the first plant seed and the second plant seed. After emergence of the seedling of the first plant seed and the seedling of the second plant seed, then applying an herbicide to the seedlings. The herbicide selectively targets the unique genetic characteristic of the second plant seed to destroy the seedling of the second plant seed without destroying the seedling of the first plant seed.

According to yet another form of the present invention, a method is provided for planting seeds to provide sufficient emergence energy to facilitate emergence of plants from a growth medium and subsequently destroying a portion of emerged plants to optimize growth potential of the growth medium. The method includes planting a plurality of seeds within a growth medium such that two or more seeds are positioned next to one another to cooperate as they grow and provide energy to emerge though a crust of the growth medium. The plurality of seeds include a mixture of a first seed type having a preferred genetic profile and a second seed type having a less-preferred genetic profile. Preferably, one of the first seed type and one of the second seed type are next to one another within the soil. Upon emergence of seedlings of the first seed type and seedlings of the second seed type through the growth medium, applying a selective herbicide to the growth medium to selectively destroy the seedlings of one of the seed types. For example, targeting the seedlings of the second seed type as the first seed type is resistant to the selective herbicide due to a characteristic of the first seed type's preferred genetic profile and the second seed type is susceptible to the selective herbicide due to a characteristic of the second seed type's less-preferred genetic profile.

According to another form of the present invention, a package is provided for uniformly containing and planting of agricultural products. The package includes a container defining a hollow body that contains an agricultural product disposed inside of the hollow body of the container. The container is dissolvable within a growth medium, such as field soil, to expose the agricultural product to the growth medium after the container has been planted in the soil. Agricultural products disposed in the hollow body may include, but are not limited to, viable plant seeds, fungicides, insecticides, fertilizers, biological products, microbial inoculants, or plant growth regulators. The container provides a uniform exterior shape to facilitate consistent and uniform engagement by planting equipment, thus improving consistency and uniformity of dispensing and planting in the soil as compared to non-uniform plant seeds which may yield inconsistent planting results due to their non-uniform shapes. The package allows for increased amounts of non-seed products to be planted alongside seeds, as compared to the amount achievable by coating seeds with such a product, as a seed is only capable of accepting and retaining a certain amount of coating along its exterior.

In one aspect, the agricultural product is a viable plant seed. The package may further include a second plant seed disposed inside of the hollow body of the container. One of the seeds may include a genetic characteristic that is not present in the other seed. The package having two seeds with different genetic characteristics may also contain non-seed agricultural products disposed inside of the hollow body of the container along with the seeds. The different genetic characteristics exhibited by the seeds within the package allow an operator to selectively destroy one of the seedlings at a desired time during the germination and growth cycle.

According to yet another form of the present invention, a planting device is provided for planting a plurality of agriculture products at a plurality of locations within a growth medium. The planting device includes a circular plate and a plurality of engagement elements disposed around a circumference of the circular plate. Each of the engagement elements is configured to selectively engage at least one chosen from a seed, a plurality of seeds, and a seed package such as a capsule. The planting device is configured to subsequently dispense the engaged agricultural product at a desired location within a growth medium, such as soil. In one aspect, a vacuum system is in fluid communication with each of the engagement elements to facilitate the selective engagement of the at least one chosen from a seed, a plurality of seeds, and a seed package.

Accordingly, the method of planting, the agricultural product package, and the planting device provide improvements to the planting, emergence, and yield of a crop. Planting of two seeds alongside one another allows for a combination of emergence energy of both seedlings to emerge together through a soil, such as a soil with a crust formed thereon. Selectively destroying one of the emerged seedlings reduces the overall population of the crop in a manner that improves the overall yield of the crop. The agricultural product package and the planting device provide for improved consistency and uniformity during the planting process which thereby improves the yield of the crop. The method, package, and planting device may be utilized to plant non-seed agricultural products alongside viable plant seeds such that increased amounts of non-seed products are available to the seeds after planting.

These and other objects, advantages, purposes and features of this invention will become apparent upon review of the following specification in conjunction with the drawings.

DESCRIPTION OF THE PREFERRED EMBODIMENTS

Figure 11:
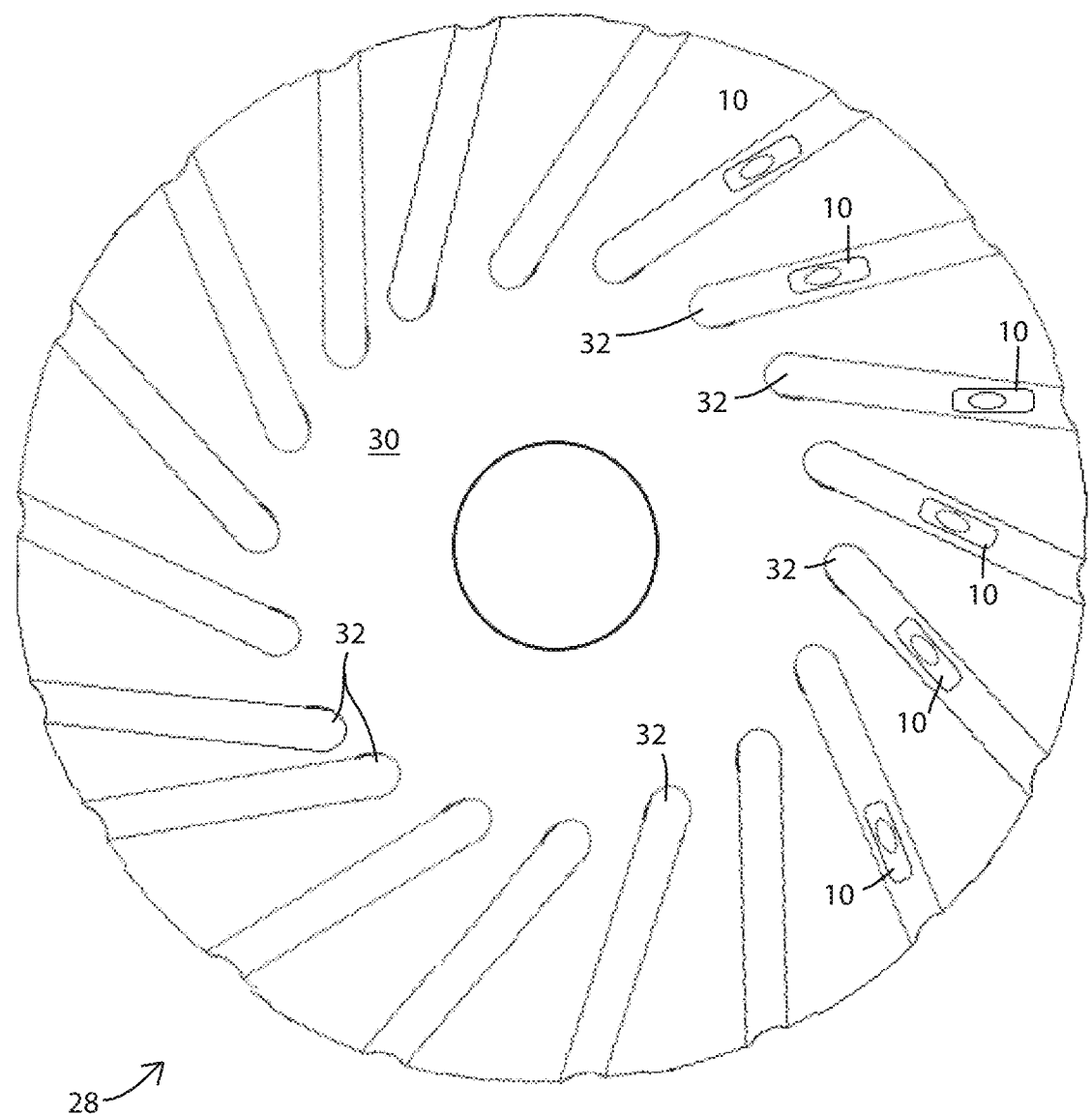
FIG. 11 is a side view of a planting device in accordance with the present invention, depicted with agricultural product planting packages selectively engaged in a plurality engagement elements.

Referring now to the drawings and the illustrative embodiments depicted therein, a method 100 and a container 12 (FIGS. 1 and 2) are provided for improving emergence rates of seedlings and improving yield rates of crops planted in a growth medium, such as field soil. The method 100 provides improved emergence rates by providing additional emergence energy through the soil proximate a seed planted in the soil. The method 100 includes planting multiple seeds adjacent to one another, and after emergence, selectively destroying or culling at least one of the adjacent seeds to reduce the population of plants. Overpopulation of plants may lead to decreased yield and selectively destroying at least one of the multiple seeds may increase yield of the crop. A container or capsule 12 is provided for containing one or more agricultural product, including seeds and fertilizers (FIGS. 2 and 5-10). The capsule 12 may contain a plurality of seeds having different genetic traits, characteristics, or profiles (e.g. resistance to certain herbicides, such as ROUNDUP® or LIBERTY® for example). By containing multiple seeds in a capsule 12, the operator planting the seeds can ensure that the plurality of seeds are consistently and uniformly planted in a field. While the capsule 12 is particularly useful for planting a plurality of seeds in close proximity to one another, the capsule 12 is also useful for encapsulating a single seed or multiple seeds along with fertilizers or other non-seed products 20 to plant seeds and fertilizers proximate one another as the seeds are planted (FIGS. 5-10). A planting device 28 is contemplated for consistently engaging a container or capsule 12 and uniformly dispensing and planting the container 12 in the soil (FIG. 11). The planting device 28 may be a planter plate or disc 30 that includes a vacuum system to facilitate engagement of the container 12 by the plate 30. The capsule 12 and planting device 28 each provide improvements in plant spacing and planting consistency to provide enhanced yields.

Figure 1:
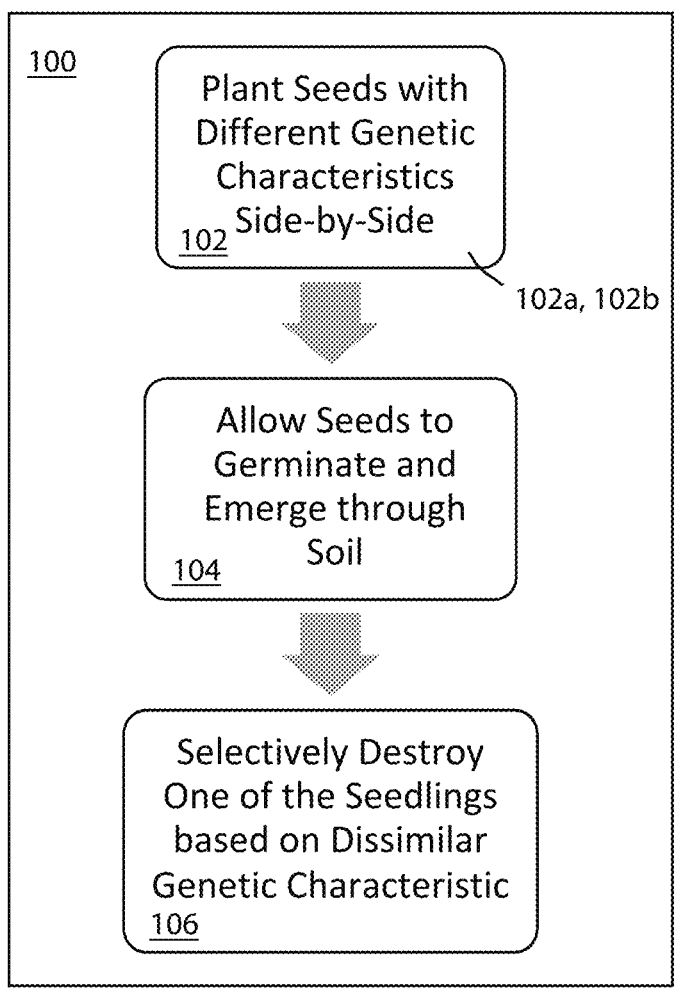
FIG. 1 is a diagram depicting a method for planting agricultural products for improved emergence and improved yield, in accordance with the present invention.
Figure 2:
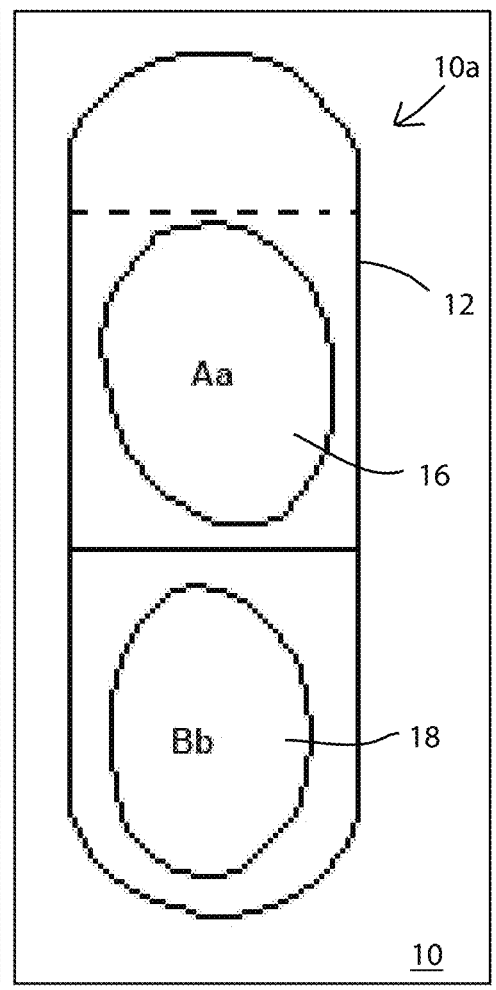
FIG. 2 is a side elevation view of an agricultural product planting package having two seeds of differing genetic characteristics, in accordance with the present invention.

In the illustrated embodiment of FIG. 1, a method 100 is provided for planting of seeds for improved emergence rates and yield rates. The method includes planting 102 at least two seeds alongside one another (FIGS. 1 and 4A). The planting 102 of at least two seeds includes planting 102a a first viable seed 16 at a first location in a growth medium, such as field soil 14, and substantially simultaneously planting 102b a second viable seed 18 substantially alongside the first seed 16 at the first location in the soil such that the first seed 18 and the second seed 16 are substantially alongside or next to one another. The spacing distance of the first seed 16 and the second seed 18 is substantially alongside or next to one another such that both seeds work together to emerge or break through the soil during growth from seed stage 16, 18 (FIGS. 2-4) to seedling stage 16a, 18a (FIGS. 4B-4D). The planting 102 may be accomplished by planting the seeds 16, 18 independently or by providing the first seed 16 and the second seed 18 in a package, such as inside of a capsule 12 (FIG. 2), which will be discussed in further detail below. The method 100 includes allowing time 104 for the seeds to germinate and break-through or emerge through the soil into seedlings (FIGS. 1 and 4B). Upon emergence of each seedling 16a, 18a, the method 100 includes selectively destroying 106 either the first seedling or the second seedling to selectively decrease the population of plants in a field (FIG. 1). In the illustrative embodiment of FIG. 4C, the first seedling 16a is a desired seedling that is allowed to mature and the second seedling 18a is a sacrificial seedling that is targeted and destroyed, however, it will be appreciated that either of the seedlings 16a, 18a may be targeted. The method 100 is repeated during the planting and growth of seeds at each planting location in the field 13 to improve overall emergence rates through the soil and to then selectively remove the excess population of plants to thereby increase yield of the crop.

The first seed 16 and the second seed 18 may include or represent different genetic profiles, traits, and characteristics that are not present in the other seed (shown in FIGS. 2-4D) as Aa and Bb in the respective seeds/seedlings). For example, the first seed 16 may be ROUNDUP READY® such that it is resistant to ROUNDUP® herbicide and the second seed 18 may be LIBERTY LINK® such that it is resistant to LIBERTY® herbicide. In this example, an operator could then administer ROUNDUP® herbicide to the field to selectively destroy 106 the seedling 18a that is not resistant to ROUNDUP®, thereby enabling the ROUNDUP READY® seedling 16a to mature into an adult plant within a desired adequate growing area. Thus, the seeds planted in the field and allowed to mature will be adequately spaced, based on soil properties and nutrient requirements for the particular plant, to achieve improved yield of the crop.

It is contemplated that the selective destroying or culling of one of the seedlings may be performed manually, such as by hand by an agriculture worker. For example, the genetic characteristic differences of the first seed and the second seed may exhibit different and distinct visual characteristics of the seedlings or plants that emerge from the particular seed types. Upon emergence of the seedlings, a worker may then selectively destroy only those plants that have the visual characteristics of the chosen sacrificial plant.

Figure 3:
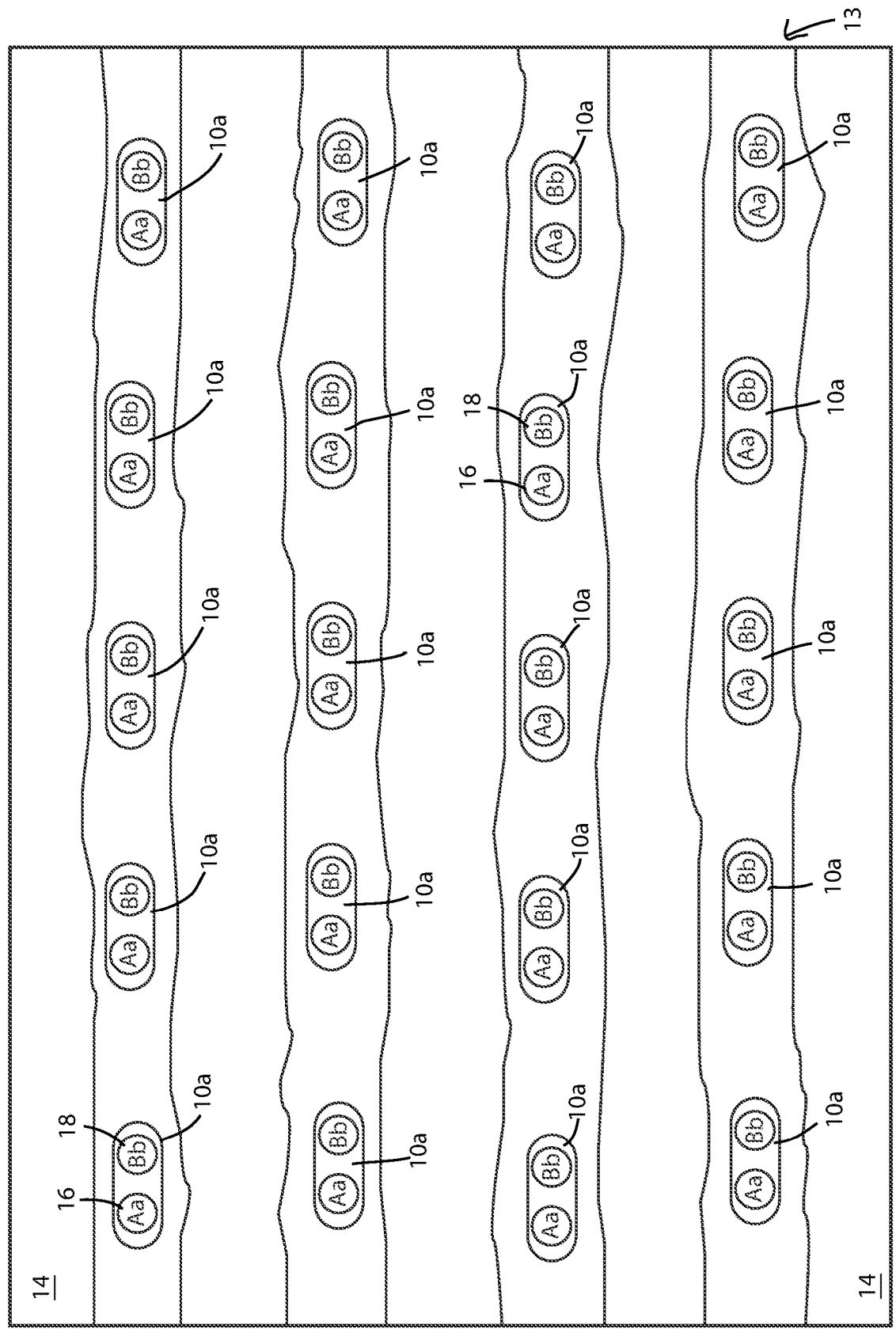
FIG. 3 is a top view of a plurality of the agricultural product planting package of FIG. 2 planted in spaced arrangement within a growth medium.
Figure 4A:
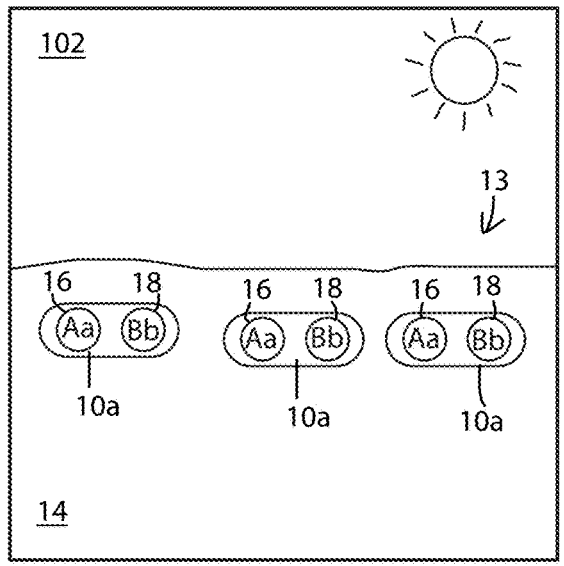
FIGS. 4A-4D are side elevation views of a portion of a field, depicting sequential steps of a method for planting a plurality of the agricultural product planting package of FIG. 2 for improved emergence and improved yield.
Figure 4B:
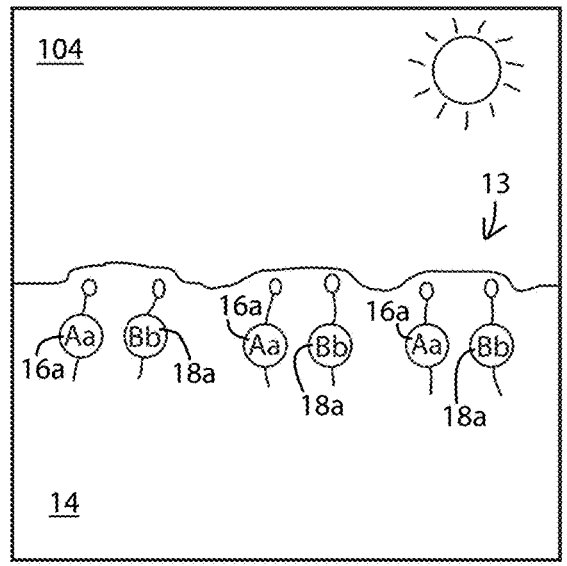
Figure 4C:
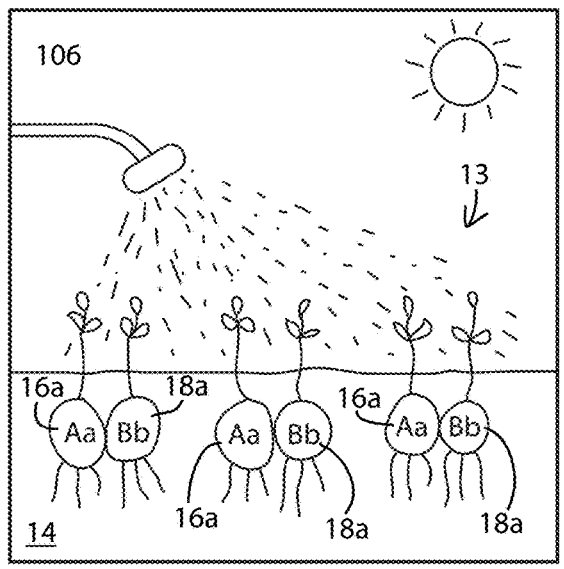
Figure 4D:
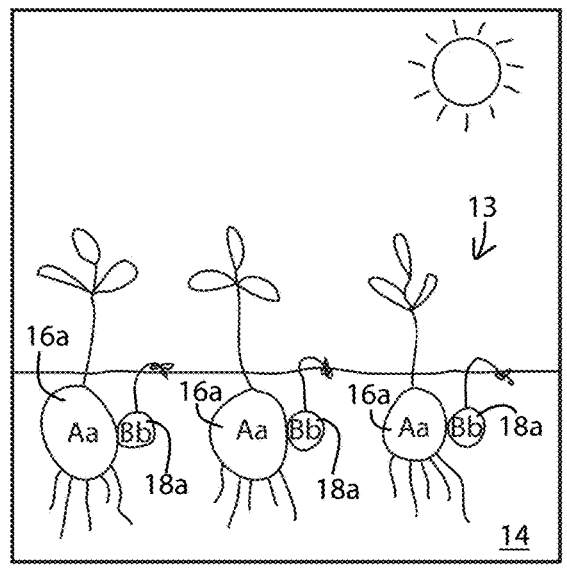

In the illustrated embodiments of FIGS. 2-4A and 5-11, a package 10 (and exemplary variants thereof 10a, 10b, etc.) is provided for uniformly containing agricultural products to be planted in a growth medium, such as soil 14 in a field 13. The package 10 is defined by a container 12 having a hollow body. The container 12 may be a dissolvable capsule similar to that used for orally administered pharmaceuticals. Preferably, the container 12 is dissolvable within a growth medium, such as soil 14, to expose the agricultural product initially encapsulated therein to the growth medium 14 (FIGS. 3 and 4A). The dissolvable material of the container 12 is preferably harmless to the growth medium 14 and the agricultural product disposed therein. Optionally, the dissolvable material defining the capsule may include agriculture products such as fertilizers or other biological matter. The package 10 provides various advantages over loose seed planting, including but not limited to, uniform placement of multiple seeds alongside one another (if desired), improved emergence force by planting multiple seeds alongside each other to push through the soil surface together, improved fertilization and feeding of a seed by providing more fertilizer or plant food next to the seed during planting than can be achieved by coating the seed alone, and improved dispensing and planting consistency and uniformity by ensuring that a planting equipment consistently engages and dispenses the uniform packages 10. It should be understood that loose seeds are not uniformly shaped and may not be consistently engaged by planting equipment. The uniform shape and size of the package 10 reduces or substantially eliminates inconsistencies during planting by eliminating any need for the planting device to directly engage the non-uniform seeds during the planting process.

As illustrated in FIGS. 2 and 5-10, the package 10 may contain various agricultural products and combinations thereof. In the illustrative embodiment of FIG. 2, a genetically diverse package 10a contains a first seed 16 and a second seed 18 disposed inside the hollow body of the container 12. Preferably, one of the seeds 16, 18 includes a genetic characteristic that is not present in the other seed, with these different genetics depicted as Aa and Bb within the respective seeds 16, 18 (FIGS. 2-4A). The differences in genetic characteristics of the seeds 16, 18 enable an operator to administer an agricultural product, such as an herbicide, to seedlings 16a, 18a emerging from the seeds 16, 18 to selectively destroy the seedling that lacks the genetic characteristics resistant to the administered product. Preferably, the seeds 16, 18 encapsulated in the package 10a are allowed to germinate and emerge through the soil 14 before being selectively destroyed.

Figure 5:
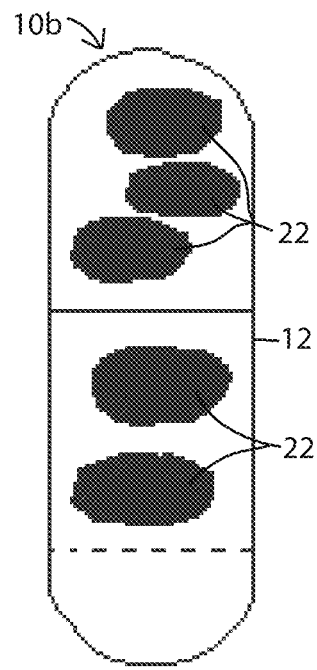
FIG. 5 is a side elevation view of another agricultural product planting package having a plurality of wheat seeds disposed inside of the package.
Figure 6:
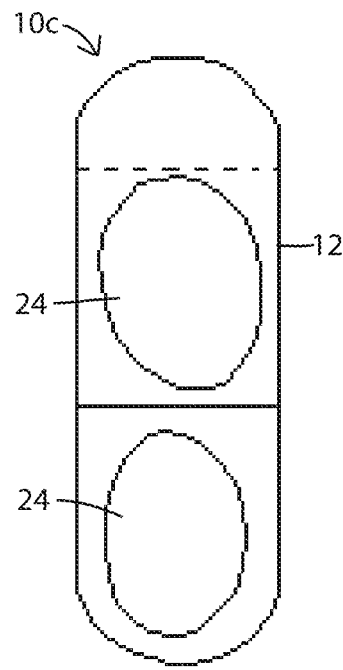
FIG. 6 is a side elevation view of another agricultural product planting package having a two soybean seeds disposed inside of the package.
Figure 7:
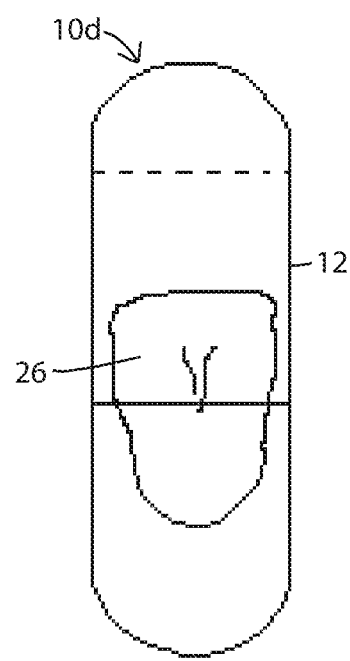
FIG. 7 is a side elevation view of another agricultural product planting package having a corn seed disposed inside of the package.

In the illustrative embodiments of FIGS. 5-6, additional packages 10b and 10c are provided and each contain a plurality of similar seeds that exhibit the same genetic characteristics for the purpose of uniformly providing a desired number of seeds at a planting location. For example, multiple wheat seeds 22 are disposed in the capsule 12 of package 10b (FIG. 5) and multiple soybean seeds 24 are disposed in the capsule 12 of package 10c (FIG. 6). In illustrative embodiment of FIG. 7, a single seed package 10d contains only a single seed, such as a corn seed 26, and no added non-seed products (see also FIG. 11). In this case, the single seed package 10d is provided for ensuring uniform engagement, dispensing, and planting of seeds 16 in the growth medium 14.

Figure 8:
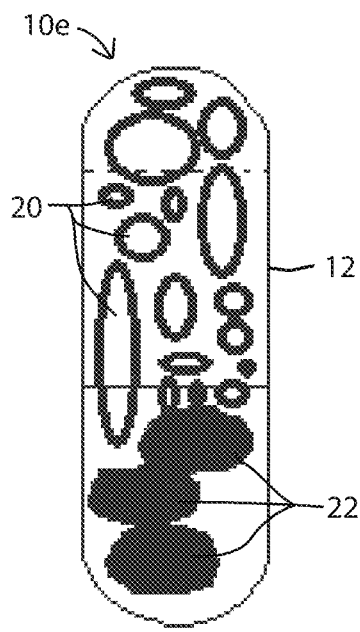
FIG. 8 is a side elevation view of another agricultural product planting package having a plurality of wheat seeds and other agricultural products disposed inside the package.
Figure 9:
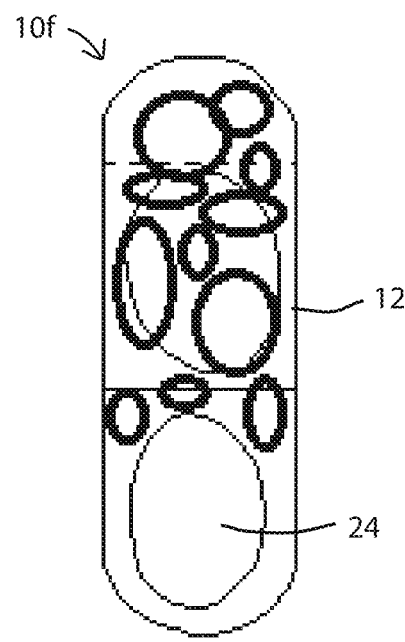
FIG. 9 is a side elevation view of another agricultural product planting package having two soybean seeds and other agricultural products disposed inside the package.
Figure 10:
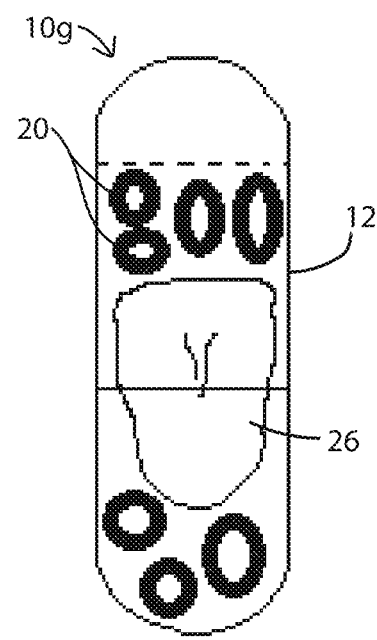
FIG. 10 is a perspective view of another agricultural product planting package having a corn seed and other agricultural products disposed inside the package.

As shown in the illustrated embodiments of FIGS. 8-9, mixed product and multiple seed packages 10e and 10f are provided and each contains multiple seeds, and at least one non-seed agricultural product 20 inside of the hollow body of the container 12. For example, multiple wheat seeds 22 and multiple non-seed products 20 are disposed in the capsule 12 of package 10e (FIG. 8) and multiple soybean seeds 24 and multiple non-seed products 20 are disposed in the capsule 12 of package 10f (FIG. 9). In illustrative embodiment of FIG. 10, a mixed product and single seed package 10g is provided and contains only a single seed, such as a corn seed 26 and at least one non-seed agricultural product 20. The non-seed agricultural product 20 may include one or more a various products, such as fungicides, insecticides, fertilizers, biological products, microbial inoculants, and/or plant growth regulators. The packages 10e, 10f, and 10g containing a seed and non-seed agricultural product 20 each enable increased amounts of non-seed products 20 to be planted directly alongside the seed than can be accomplished with traditional methods, such as coating the seed in the desired product 20.

A planting device 28 is provided for planting a plurality of seeds and/or non-seed agricultural products at a single location, as shown in illustrative embodiment of FIG. 11. The planting device 28 may be configured to plant seed packages 10, such as capsules 12, containing a single seed, a plurality of seeds, and/or other non-seed agricultural product (FIG. 11). The planting device 28 includes a circular planting plate 30 defining a plurality of capsule engagement elements 32 disposed around the circumference of the circular plate 30. Each of the capsule engagement elements 32 is configured to receive a capsule 12 and subsequently dispense the capsule 12 at a desired location, such as within field soil 14. The planting device 28 may further include additional engagement recesses to selectively receive single seeds. The planting device 28 enables consistent engagement of capsules 12 and/or seeds to properly singulate the capsules 12 and/or seeds for proper spacing in the soil 14. Preferably, the planting device 28 is adaptable for use with a variety of different planting equipment, such as planter meters. The planting device 28 may include a vacuum system in fluid communication with each capsule engagement element 32 and/or engagement recess to facilitate selective engagement of the capsules 12 and/or seeds 16 within the capsule engagement elements 32 or engagement recesses and to then facilitate selective deposition of the capsules 12 and/or seeds in the soil. To singulate refers to retrieving or engaging a single product, such as a capsule or a seed, from a batch of similar products (e.g. a bin full of capsules or seeds) and dispensing the single product in an individual manner. For example, planting equipment may utilize a planting plate and a planter meter to engage or grab one seed from a bin of seeds and to release or dispense the seed down a seed tube of the planting equipment to then be introduced to the soil.

Thus, a method, a container, and a planting device are provided for improving seedling emergence from seeds in a field of soil and improving yield of plants in the field. The method includes selectively planting at least two seeds next to one another within the soil to provide adequate emergence energy to emerge through the soil, waiting for the seedlings to emerge through the soil, and then selectively destroying one of the at least two seedlings that emerged to provide proper or desired spacing between plants in the field. A capsule is provided to contain one or more seeds and/or non-seed agricultural products to facilitate uniform and consistent planting of seeds and/or other products next to one another within a field and to facilitate uniform and consistent dispensing of the seeds by a planting device. A planting device, such as a planter plate, is provided to consistently and uniformly engage the capsules and/or seeds during planting to consistently and uniformly plant seeds and/or other products within the field.

Changes and modifications in the specifically described embodiments can be carried out without departing from the principles of the present invention which is intended to be limited only by the scope of the appended claims, as interpreted according to the principles of patent law including the doctrine of equivalents.

The invention claimed is:

1. A method for planting of seeds for improved emergence rates and yield rates, said method comprising:
   selecting a plurality of desired seeds and a plurality of sacrificial seeds based on known genetic characteristics of the seeds;
   planting the plurality of desired seeds in a spaced arrangement in a growth medium;
   planting one of the plurality of sacrificial seeds alongside one of the plurality of desired seeds such that the emergence energy of a desired seedling from the desired seed combines with the emergence energy of a sacrificial seedling from the sacrificial seed alongside the desired seedling as the seedlings grow to break through a crust of the growth medium; and
   upon emergence of the desired seedling and sacrificial seedling through the crust, selectively destroying only the sacrificial seedling.

2. The method of claim 1, wherein each of the desired seeds comprises a genetic characteristic that is not present in the sacrificial seeds.

3. The method of claim 2, wherein said selectively destroying only the sacrificial seedling comprises selectively targeting the sacrificial seedling to selectively destroy the sacrificial seedling based on the genetic characteristic that is not present in the sacrificial seeds.

4. The method of claim 3, wherein said selectively targeting the sacrificial seedling is performed by applying a herbicide to the desired seedling and the sacrificial seedling, wherein the desired seedling is resistant to the herbicide and the sacrificial seedling is susceptible to the herbicide due to the lack of the genetic characteristic that is present in the desired seeds.

5. The method of claim 1, wherein the desired seed and the sacrificial seed planted alongside one another are contained together in a capsule such that said planting the desired seed is simultaneous with said planting the sacrificial seed.

* * * * *